US009192772B1

(12) United States Patent
Tsukamoto et al.

(10) Patent No.: US 9,192,772 B1
(45) Date of Patent: Nov. 24, 2015

(54) PORTABLE MEDICAL POWER SYSTEM (75) Inventors: Hisashi Tsukamoto, Santa Clarita, CA (US); Clay Kishiyama, Burbank, CA (US)

(73) Assignee: Quallion LLC, Sylmar, CA (US)

( * ) Notice: Subject to any disclaimer, the term of this patent is extended or adjusted under 35 U.S.C. 154(b) by 2541 days.

(21) Appl. No.: 10/881,158

(22) Filed: Jun. 29, 2004

(51) Int. Cl.
*A61N 1/378* (2006.01)

(52) U.S. Cl.
CPC .................................. *A61N 1/3787* (2013.01)

(58) Field of Classification Search
CPC ............ A61N 1/3787; A61N 1/36125; A61N 1/37229; A61N 1/3756; A61N 1/37223; A61N 1/37217; A61N 1/375; A61N 1/0526; H02J 7/025; H02J 5/005; H02J 7/0052; H02J 7/007; A61B 5/0031; A61B 2560/0219
USPC .......................................... 607/32–34, 60–61
See application file for complete search history.

(56) References Cited

U.S. PATENT DOCUMENTS

| | | |
|---|---|---|
| 3,694,729 A | 9/1972 | Jones |
| 4,665,896 A | 5/1987 | LaForge et al. |
| 4,748,344 A | 5/1988 | Sing |
| 4,851,756 A | 7/1989 | Schaller et al. |
| 4,977,899 A | 12/1990 | Digby et al. |
| 5,211,321 A | 5/1993 | Rodriguez |
| 5,289,046 A | 2/1994 | Gregorich et al. |
| 5,411,537 A * | 5/1995 | Munshi et al. .................. 607/33 |
| 5,455,637 A | 10/1995 | Kallman et al. |
| 5,455,638 A | 10/1995 | Kallman et al. |
| 5,574,622 A | 11/1996 | Brown |
| 5,610,496 A | 3/1997 | Hofbauer et al. |
| 5,733,313 A * | 3/1998 | Barreras et al. .................. 607/33 |
| 5,835,185 A | 11/1998 | Kallman et al. |
| 5,850,113 A | 12/1998 | Weimer et al. |
| 5,861,684 A | 1/1999 | Slade et al. |
| 5,900,720 A | 5/1999 | Kallman et al. |
| 5,914,542 A | 6/1999 | Weimer et al. |
| 5,929,597 A | 7/1999 | Pfeifer et al. |
| 5,973,476 A | 10/1999 | Irvin |

(Continued)

FOREIGN PATENT DOCUMENTS

| | | |
|---|---|---|
| EP | 1406692 | 4/2004 |
| WO | WO 01/83029 A1 | 11/2001 |

(Continued)

OTHER PUBLICATIONS

Mukainakano, H., U.S. Appl. No. 10/639,178, filed Sep. 30, 2003.

(Continued)

*Primary Examiner* — Rex R Holmes (74) *Attorney, Agent, or Firm* — Gavrilovich, Dodd & Lindsey, LLP (57) ABSTRACT

Disclosed is a medical power system for powering an implantable medical device including an implantable rechargeable battery pack, a wearable power source, a power cart, and an external power supply. The system may be used in three modes: 1) Fully disconnected (powered by implanted battery only); 2) Power provided by a wearable power source and/or a portable wheeled power cart via an inductive link, and 3) Nonportable power provided by a non-portable source such as an AC outlet with an uninterruptible power supply. The system includes automatic choice of the optimum source of power depending on the circumstances, and greatly increases "untethered time" a bionic-dependent patient may spend.

19 Claims, 5 Drawing Sheets

(56) References Cited

U.S. PATENT DOCUMENTS

| | | | |
|---|---|---|---|
| 5,996,115 A | 12/1999 | Mazelsky | |
| 6,106,971 A | 8/2000 | Spotnitz | |
| 6,265,846 B1 | 7/2001 | Flechsig et al. | |
| 6,272,781 B1 | 8/2001 | Resnick | |
| 6,358,281 B1* | 3/2002 | Berrang et al. | 623/10 |
| 6,388,422 B1 | 5/2002 | Lew | |
| 6,431,044 B2 | 8/2002 | Poole | |
| 6,445,162 B1 | 9/2002 | Mukainakano | |
| 6,476,581 B2 | 11/2002 | Lew | |
| 6,515,456 B1 | 2/2003 | Mixon | |
| 6,528,970 B1 | 3/2003 | Liu et al. | |
| 6,531,847 B1 | 3/2003 | Tsukamoto et al. | |
| 6,538,414 B1 | 3/2003 | Tsuruga et al. | |
| 6,549,807 B1* | 4/2003 | Kroll | 607/34 |
| 6,559,621 B2 | 5/2003 | Corless et al. | |
| 6,563,290 B2 | 5/2003 | Sakakibara et al. | |
| 6,563,291 B2 | 5/2003 | Tamura et al. | |
| D475,680 S | 6/2003 | Krieger et al. | |
| 6,580,251 B2 | 6/2003 | Takeuchi | |
| 6,584,329 B1 | 6/2003 | Wendelrup et al. | |
| 6,586,850 B1 | 7/2003 | Powers | |
| 6,586,912 B1 | 7/2003 | Tsukamoto et al. | |
| 6,639,381 B2 | 10/2003 | Tamura et al. | |
| 6,845,267 B2* | 1/2005 | Harrison et al. | 607/3 |
| 2002/0047309 A1 | 4/2002 | Droppo et al. | |
| 2002/0076071 A1 | 6/2002 | Single | |
| 2002/0185916 A1 | 12/2002 | Baron et al. | |
| 2003/0020332 A1 | 1/2003 | Giannopoulos et al. | |
| 2003/0052547 A1 | 3/2003 | Fischer et al. | |
| 2003/0085621 A1 | 5/2003 | Potega | |
| 2003/0085684 A1 | 5/2003 | Tsukamoto et al. | |
| 2003/0111908 A1 | 6/2003 | Christensen | |
| 2003/0114899 A1* | 6/2003 | Woods et al. | 607/60 |
| 2003/0129498 A1 | 7/2003 | Tsukamoto | |
| 2003/0180624 A1 | 9/2003 | Oh et al. | |
| 2003/0180625 A1 | 9/2003 | Oh et al. | |
| 2003/0191504 A1* | 10/2003 | Meadows et al. | 607/33 |
| 2003/0195581 A1* | 10/2003 | Meadows et al. | 607/29 |
| 2004/0004464 A1 | 1/2004 | Tsukamoto et al. | |
| 2004/0225338 A1* | 11/2004 | Lebel et al. | 607/60 |
| 2005/0075693 A1* | 4/2005 | Toy et al. | 607/60 |
| 2005/0075694 A1* | 4/2005 | Schmeling et al. | 607/61 |
| 2005/0075696 A1* | 4/2005 | Forsberg et al. | 607/61 |
| 2005/0075697 A1* | 4/2005 | Olson et al. | 607/61 |
| 2005/0075698 A1* | 4/2005 | Phillips et al. | 607/61 |
| 2005/0075699 A1* | 4/2005 | Olson et al. | 607/61 |
| 2005/0075700 A1* | 4/2005 | Schommer et al. | 607/61 |

FOREIGN PATENT DOCUMENTS

| | | |
|---|---|---|
| WO | WO 02/089904 A2 | 11/2002 |
| WO | WO 02/089904 A3 | 11/2002 |
| WO | WO 03/041208 A1 | 5/2003 |
| WO | WO 03/058746 A1 | 7/2003 |
| WO | WO 03/061032 A3 | 7/2003 |
| WO | WO 03/083970 A1 | 10/2003 |
| WO | WO 03/083971 A1 | 10/2003 |
| WO | WO 03/083972 A1 | 10/2003 |
| WO | WO 03/083973 A1 | 10/2003 |
| WO | WO 03/083974 A1 | 10/2003 |
| WO | WO 03/090299 A1 | 10/2003 |
| WO | WO 2004/014214 A2 | 2/2004 |
| WO | WO 2004/027955 A2 | 4/2004 |

OTHER PUBLICATIONS

Kishiyama, C. et al., U.S. Appl. No. 10/676,203, filed Feb. 6, 2004.
Parkhouse, L., U.S. Appl. No. 10/773,651, filed Sep. 30, 2003.
Altieri, F., et al.; Implantable Ventricular Assist Systems; *Artif Organs.*, vol. 11, No. 3, 1987. International Society for Artificial Organs.
Dowling, R. et al; The AbioCor Implantable Replacement Heart; *Ann Thorac Surg*; 2003; 75:S98-9. The Society of Thoracic Surgeons; Elsevier, Inc.
El-Banayosy, A. et al; Preliminary Experience With the LionHart Left Ventricular Assist Device in Patients With End-Stage Hear Failure; *Ann Thorac Surg*; 2003;75:1469-75. The Society of Thoracic Surgeons; Elsevier Science, Inc.
Honda, H., et al.; Selection of a Rechargeable Internal Back-up Battery for a Totally Implantable Artificial Heart; *ASAIO Journal*, 1999.
Kim, W.E., et al.; Intelligent Li Ion Battery Management Based on a Digital Signal Processor for a Moving Actuator Total Artificial Heart.
Lanmüller, H..; Useful Applications and Limits of Battery Powered Implants in Functional Electrical Stimulations; *Artificial Organs*, 21(3):210-212; Blackwell Science, Inc., Boston.
Maclean, G.; Comparison of Rechargeable Lithium and Nickel/Cadmium Battery Cells for Implantable Circulatory Support Devices; *Artificial Organs*; 18(4):331-334, Blackwell Scientific Publications, Inc., Boston.
Maclean, G.; Evaluation of Nickel—Cadmium Battery Paths for Mechanical Circulatory Support Devices; *ASAIO Journal* 1993.
Maclean, G; The Effect of Pulsatile Power Loads on Nickel/Cadmium Battery Cells for Mechanical Circulatory Support Devices; *ASAIO Journal* 1994.
Mussivand, T.; A Transcutaneous Energy and Information Transfer System for Implanted Medical Devices.
Mussivand, T.; Transcutaneous Energy Transfer System Performance Evaluation; *Artificial Organs*, 17(11):940-947, Blackwell Scientific Publications, Inc., Boston.
Okamoto, E., et al.; Feasibility of a Nickel-Metal Hydride Battery for Totally Implantable Artificial Hearts.
Powers, R., et al.; Life Testing of Implantable Batteries for a Total Artificial Heart; *ASAIO Journal* 1993.
Shiba, K., et al.; A Transcutaneous Energy System with Rechargeable Internal Back-up Battery for a Totally Implantable Total Artificial Heart; *ASAIO Journal* 1999.
Tempower http://www.tempower.net.futuresite.register.com/_wsn/page4.html 2 Pages (date unknown).
Kohler Event Services http://www.kohlereventservices.com/equip_service/power/power_distribution.html 1 Page (date unknown).
Cal-Distro, Heavy Duty Outdoor/Construction Series, Power Distribution Equipment, http://www.cal-distro.com/, 2 pages (date unknown).
Cal-Distro, Heavy Duty Outdoor/Construction Series, Heavy Duty, http://www.cal-distro.com/heavy_duty.htm 2 pages (date unknown).
Cal-Distro, Heavy Duty Outdoor/Construction Series, Heavy Duty 2, http://www.cal-distro.com/heavy_duty_2.htm, 2 pages (date unknown).

* cited by examiner

PORTABLE MEDICAL POWER SYSTEM

REFERENCE TO PRIOR FIELD APPLICATIONS

This invention is related to U.S. patent application Ser. No. 10/798,499, filed Mar. 10, 2004, entitled "Power System", which is incorporated by reference in its entirety.

FIELD

This invention relates to portable medical power systems, and more particularly to a system for powering an implantable medical device.

BACKGROUND

Electronic biomedical devices such as pacemakers, defibrillators, left ventricular assist devices (LVADs), cochlear implants, diaphragm pacemakers, artificial retinas, glucose sensors, insulin pumps, and neuromuscular stimulators are significantly improving both the length and quality of life for millions of people. New implantable devices are under development to treat a myriad of disabilities and ailments including spinal cord paralysis, epilepsy, diabetes, blindness, and deafness. Power sources used for many such portable devices may require large current drains, and thus require relatively large size batteries for extended use. Additionally, life-critical implantable medical devices require ultra-reliable power sources.

It has been widely taught that implantable, self-sufficient energy sources are impractical for high-power devices such as circulatory assist devices (See e.g. U.S. Pat. No. 4,665,896 to LaForge et al.). While implantable battery technology has improved significantly in recent years, it remains necessary to provide external energy sources for such high-power devices. Since artificial hearts, LVADs, diaphragm pacemakers, ventilators, and the like must have 100% reliable power sources and back-up power, these devices require that the patient either remain tethered to a fixed power source, or remain close to a fixed power source for frequent recharging of a portable power source. This severely impacts the patient's quality of live by restricting mobility.

Several devices have been developed to provide portable power suitable for various non-medical uses. For example, U.S. Pat. No. 5,211,321 to Rodriguez describes a battery and equipment vest containing batteries suitable for powering photographic equipment. Similarly, U.S. Pat. Nos. 5,929,597 and 6,106,971 teach wearable power sources for cordless devices such as power drills. U.S. Design Pat. No. D475,680 illustrates the ornamental appearance of a wheeled battery cart containing an air compressor, light, and inverter for powering a variety of electrical devices. None of these provide power for implanted medical devices.

SUMMARY

The present invention provides a portable power system with multiple energy sources suited to provide reliable and redundant power to implanted medical devices. In one aspect of the invention, the system incorporates intelligence to automatically choose which source of power is best to tap at a given time. By providing backup power and charging in various portable units, the invention affords improved mobility for patients with implantable medical devices, resulting in a vastly improved quality of life. Advantageously, the present invention provides three operating modes: 1) Fully disconnected (powered by implanted battery only); 2) Power provided by a power vest and/or a portable wheeled power cart via an inductive link; and 3) Tethered power provided by a non-portable source such as an AC outlet, preferably with an uninterruptible power supply. The flexibility and potential for increased untethered time provides significant advantages over prior art.

As used in this application, a "power outlet" can include a primary coil for inductive power transmission, an electrical power cord with a plug, an electrical socket, or any other device for transmitting power including, without limitation, conductive, capacitive, and inductive connections. As used in this application, a "power inlet" can include a secondary coil for inductive power reception, an electrical power cord with a plug, an electrical socket for receiving a plug of an electrical power cord, or any other device for receiving power including, without limitation, conductive, capacitive, and inductive connections.

In one aspect of the invention, a power system for powering an implantable medical device comprises an implantable battery pack comprising an implantable secondary battery and an energy management system for controlling power to the medical device and to the secondary battery; an implantable inlet for receiving power to charge the secondary battery; and at least two nonimplantable power sources chosen from the group consisting of: a wearable power source, a power cart, and a nonportable power source. The implantable inlet may comprise a secondary coil. The wearable power source may comprise an energy storage device; a power outlet for sending power to the implantable battery pack; and a power inlet for receiving power from either the nonportable power source, the power cart, or both. The power cart may comprise an energy storage device; a power outlet for sending power to the implantable battery pack, the wearable power source, or both; and a power inlet for receiving power from the nonportable power source. The nonportable power source may comprise a power outlet for sending power to the implantable battery pack, the wearable power source, and/or the power cart. In each case, the power outlet may comprise a primary coil, an electrical socket, or an electrical power cord with a plug.

Each of the power sources may comprise an energy management system having a controller. Alternatively or additionally, the power system may comprise a universal energy management system (UEMS), which may be located in the wearable power source, in the cart, or in a separate unit. The UEMS may comprise a power source selector for selecting a power source for powering the implantable medical device. The UEMS may comprise a charging source selector for selecting a charging source for charging a secondary battery connected to the UEMS. The UEMS may further comprise a charge controller for controlling the magnitude of the charging current to a secondary battery. The UEMS may further comprise a measuring device for measuring remaining charge in at least one battery connected to the UEMS. The remaining capacity may be determined using the method taught in U.S. Pat. No. 6,445,162, which is assigned to the assignee of the present invention and incorporated herein by reference; this method is especially suited for the implantable primary and secondary battery 14 and 12. Alternatively, the remaining capacity may be determined through means commonly known in the field; for example, if the initial capacity is known, a current counter could be employed, with a projected rate of decline of battery performance to increase accuracy. Also, for certain chemistries (e.g. lithium ion batteries) it is possible to estimate remaining capacity by measuring voltage. The power system may further comprise an indicator for communicating the measured remaining charge. The UEMS may further comprise an alarm to indicate that no power source is connected, so that the implanted device is powered only by one or more sources in the implantable battery pack. The implantable battery pack may further comprise a primary battery.

In another aspect of the invention, a method for powering a medical device comprises providing a UEMS; detachably attaching a first power source to the UEMS; detachably attaching a second power source to the UEMS; detachably attaching a powerable implantable medical device having an implantable rechargeable power source to an outlet of the UEMS; determining the optimum source of power as between the first power source, the second power source, and the implantable rechargeable battery to power the medical device; and supplying power to the medical device from the optimum source. The sources may include a tethered external power supply, a cart power source, and a wearable power source. The optimum source is the tethered source when present, and, if the tethered source is not present, the optimum source is the cart power source if it is present and adequately charged, and, if the cart power source is not adequately charged, then the wearable power source is the optimum source if it is present and adequately charged; and if the wearable power source is not present or not adequately charged, the implantable power source is used to power the medical device.

A better understanding of the present invention may be obtained by reference to the figures.

DETAILED DESCRIPTION

Figure 1:
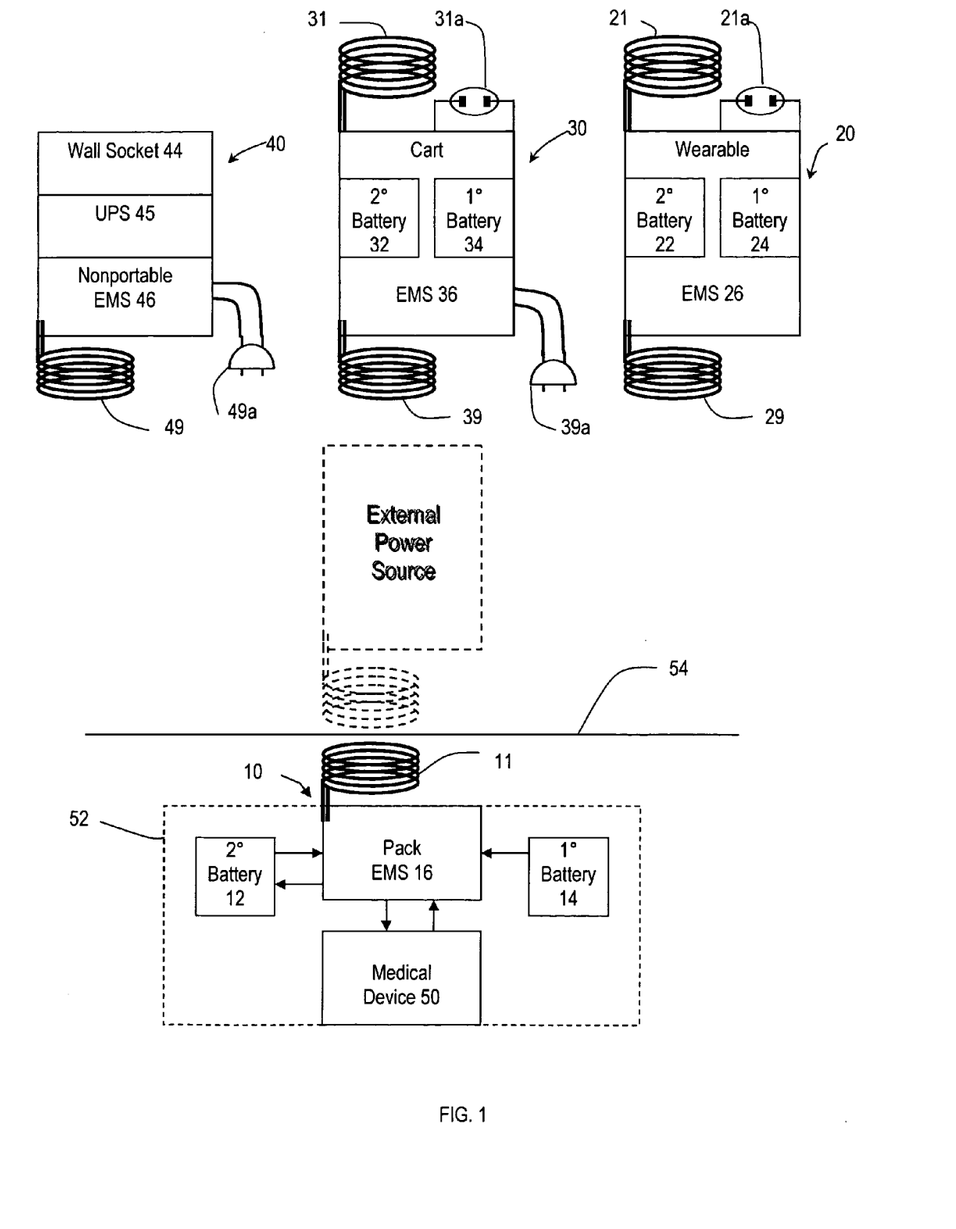
FIG. 1 is a schematic diagram of a first embodiment of the portable medical power system of the present invention having various power sources.

As shown in FIG. 1, the portable medical power system of the present invention comprises an implantable battery pack 10, and various external power sources, which may include a wearable power vest 20, a cart 30, and a tethered power source 40. The power sources of the present invention may include electrochemical storage devices and external power sources. The types of electrochemical storage devices may include primary, secondary, and any combinations thereof, and may comprise one or more cells, capacitors, hybrids of the two, fuel cells, and the like, and any combinations thereof. Furthermore, the power sources are not limited to electrochemical storage devices and may include other power sources, such as superconducting magnets and ultra-capacitors. For convenience, and for purposes of this patent, the word "battery" as used herein may refer to any or all of these electrochemical storage devices and other power sources. External power sources may include charger modules, generators, alternators, turbines, and the like, and combinations thereof. These multiple disparate power sources are flexibly managed by one or more energy management systems that optimize energy use dependent on the available power sources and the needs of the device receiving power.

The implantable battery pack 10 comprises a rechargeable (secondary) energy storage device 12, and is the most direct power source for powering an implantable device 50. It may further comprise one or more primary storage devices 14. As used herein, the term "primary battery" refers to an electrochemical device designed, engineered, and intended to operate through one discharge cycle and then be discarded without being recharged. The term "secondary battery" refers to an electrochemical device designed, engineered, and intended to operate through many discharge/charge cycles before being discarded. However, this is not meant to preclude the possibility that a primary battery may be recharged or that a secondary battery may be discarded after a single use. In a pack having both battery types available, an energy management system, Pack EMS 16, intelligently manages the selection of one as a power source for device 50. Further, once a battery is selected as a power source, the transition from one to another type of battery in response to changes in device operating and/or environmental conditions is also managed.

The implantable battery pack 10 can power the device 50 for up to 3 hours or more before recharging, depending on the load. Implantable battery pack 10 preferably can be recharged from any of the larger capacity power supply systems (vest 20, cart 30, or tethered power 40), using the method taught in U.S. patent application Ser. No. 10/639,178, filed Aug. 11, 2003, entitled "Rechargeable Implantable Battery Pack with Battery Management Circuit", which is assigned to the assignee of the present invention and incorporated herein by reference. Alternatively, any other means may be used to recharge rechargeable battery 12 of implantable battery pack 10. Pack EMS 16 can be housed together with the batteries 12 and/or 14 or in separate housings and may be housed in the same housing 52 as the medical device 50 or separately. Pack EMS 16 comprises a safety circuit and a controller. The safety circuit provides protection against overheating, and may consist of a positive temperature coefficient (PTC) circuit, which is essentially a fuse, or may include additional circuitry to protect against overcharge and/or overdischarge. The controller determines which power source to use for powering medical device 50 and manages the transition of the power source from, for example, implantable rechargeable battery 12, implantable primary battery 14, and external power, preferably via an inductive coil 11. Whenever a primary coil, such as primary coil 29 from vest power source 20, primary coil 39 from cart power source 30, or primary coil 49 from nonportable power source 40, is put into proximity of the secondary coil 11 of implantable battery pack 10, pack 10 automatically begins to recharge as needed and use power from the primary coil to power device 50.

Implantable battery pack 10 is designed to operate at 37° C., cycle for long periods of time, and have low capacity fade due to storage. Additionally, implantable battery pack 10 is highly reliable and biocompatible. Safety features may include the use of nontoxic, nonflammable electrolytes such as taught in U.S. Patent Publication US 2003-0129498 A1 and PCT Publication WO 03/058746 A1, and polysiloxanes (see Published U.S. Patent Applications US-2003-0180624 A1, US-2003-0180625 A1, Published PCT Patent Applications WO 03/083970 A1, WO 03/083971 A1, WO 03/083972 A1, WO 03/090299 A1, WO03083973 A1, WO 03083974 A1); heat absorbing material such as paraffin to protect from battery overheating (see U.S. Pat. No. 6,586,912 and Published PCT Patent Application WO 03/061032 A2); and energy dump safety circuits (see, U.S. Pat. No. 6,531,847, Published U.S. Patent Application US-2004-0004464 A1, and Published PCT Patent Application WO 03/041208 A1), all of which are assigned to the assignee of the present invention and incorporated by reference, in addition to those safety features generally known to those skilled in the art.

Wearable power source 20 is a power source for extended use. Although this portable power source is described as a vest herein, it may alternatively take the form of any garment such as a belt, backpack, waist pouch ("fanny pack"), sling, leggings, jacket, handbag, jacket, hat, or coat. Combinations of these and similar devices may be employed; however, as the capacity is increased, so too is the weight and bulk of the wearable battery packs. An advantage of the source being worn as a vest per se is that it can be designed to provide an interface with an implanted device in close proximity such as in the chest region, and allow the wearing of additional garments over the vest. Other garments may be more suitable for implantable devices located elsewhere in the body. A primary inductive coil 29 may be incorporated directly into a vest and worn such that it is directly aligned with an implanted secondary coil 11 used to charge implanted rechargeable battery 12, and power implanted medical device 50. Wearable power source 20 may include solar cells and may itself have redundant energy storage devices, as taught in U.S. patent application Ser. No. 10/676,203, filed Sep. 30, 2003, entitled "Photovoltaic Power Charging Apparatus for Implantable Rechargeable Batteries", which is assigned to the assignee of the present invention and incorporated herein by reference.

The wearable system is designed to provide up to about 12 hours or more of operation before recharging, depending on the load. Typically, a vest would power a device such as an LVAD, drawing in the range of 700 mA to 2 A. The vest 20 can incorporate several battery pouches each containing one or more batteries, and may include a combination of primary and secondary sources, 24 and 22, respectively. Alternatively, it may have only one or more secondary sources or only one or more primary sources. The vest preferably has at least one secondary source. In a wearable power source having both battery types available, an energy management system within the vest, Vest EMS 26, intelligently manages the selection of one as a power source for device 50. Further, once a battery is selected as a power source, the transition from one to another type of battery in response to changes in device operating and/or environmental conditions is also managed. Vest EMS 26 monitors each battery within the vest and controls both the flow of power from the vest and recharging of secondary batteries within the vest. By allowing both primary and secondary sources, the present invention makes it possible to combine the unique strengths of each. For example, while secondary batteries generally have high rate capability and inherent cost-savings because of their rechargeability, primary batteries typically have higher energy densities. Furthermore, secondary batteries can typically charge and discharge at rates from 0 to 5C while primary batteries typically have a preferred range of 0 to C/50. While a primary battery may operate at rates above C/50, for most primary materials, it is not generally considered cost-effective, since the battery will be used up quickly and not be rechargeable. In this regard, C refers to C-Rate, which is a measure of the current rate that a battery can put out referenced against its own capacity. A rate of 1C is equivalent to the discharge or charge rate that will fill or empty the battery completely in one hour; likewise a rate of 0.5C will last for 2 hours, whereas a rate of 2C will only last for 30 minutes. For example, a battery with a rated capacity of 10 mAh could discharge at rate of 0.1C (equivalent to 1 mA) for 10 hours or it could be charged at rate of 2C (20 mA) in 30 minutes. By allowing use of a secondary battery along with a primary battery, this system takes advantage of the intrinsic economy of rechargeable batteries while providing flexibility and improved operational time.

A primary battery and secondary battery preferably are dimensioned to allow placement of either type of battery in the same battery chamber in the vest or cart. The two types of batteries may differ geometrically in such a way as to allow the EMS to differentiate between them, while still allowing ready connectivity. For example, a feature may mechanically interact with the battery housing and EMS to indicate to the EMS that the battery is a secondary battery, whereas the primary battery has no such feature. The primary battery can utilize any primary battery chemistry, such as $CF_x$ or Zn-air, and the secondary battery can utilize any secondary battery chemistry, such as nickel metal hydride or lithium ion, including nickel-based oxides such as $LiNi_xCo_yAl_zO_2$.

The vest can be recharged by power supplied by the larger power supply systems (e.g., cart 30 or nonportable power 40). The vest 20 can recharge the rechargeable batteries 12 of the implantable battery pack 10 and operate the implanted device 50 simultaneously. In the preferred embodiment, the vest 20 provides power to the implanted battery pack 10 and/or the implanted medical device 50 by means of an inductive link comprising a primary coil 29 and a secondary coil 11. Less advantageous would be an electrical connection via an interdermal cable having a highly reliable plug (not shown). The primary coil 29 may be connected to the vest 20 via a lead wire (not shown) and placed in direct contact with the patient's skin either by an adhesive or mechanical means such as an elastic strap. The vest 20 may be manufactured using any material commonly known. For hospital environments a disposable version may be made from fiber-reinforced paper or plastic such as Tyvek®, or from any woven fabric. The vest is easy to wear, not hindering normal body movements.

Figure 4:
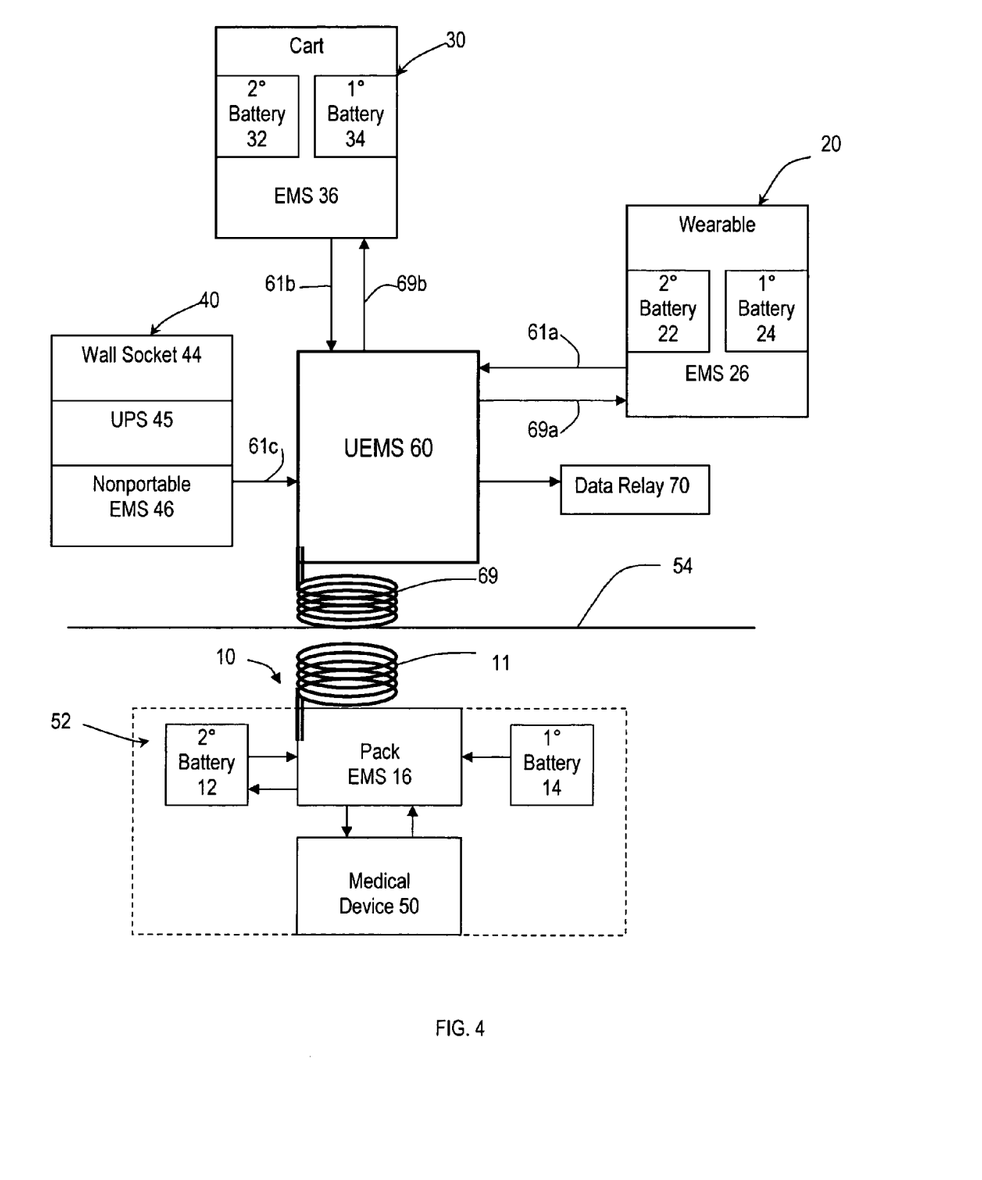
FIG. 4 is a schematic diagram of a second embodiment of the portable medical power system of the present invention having various power sources and a universal energy management system (UEMS).
Figure 5:
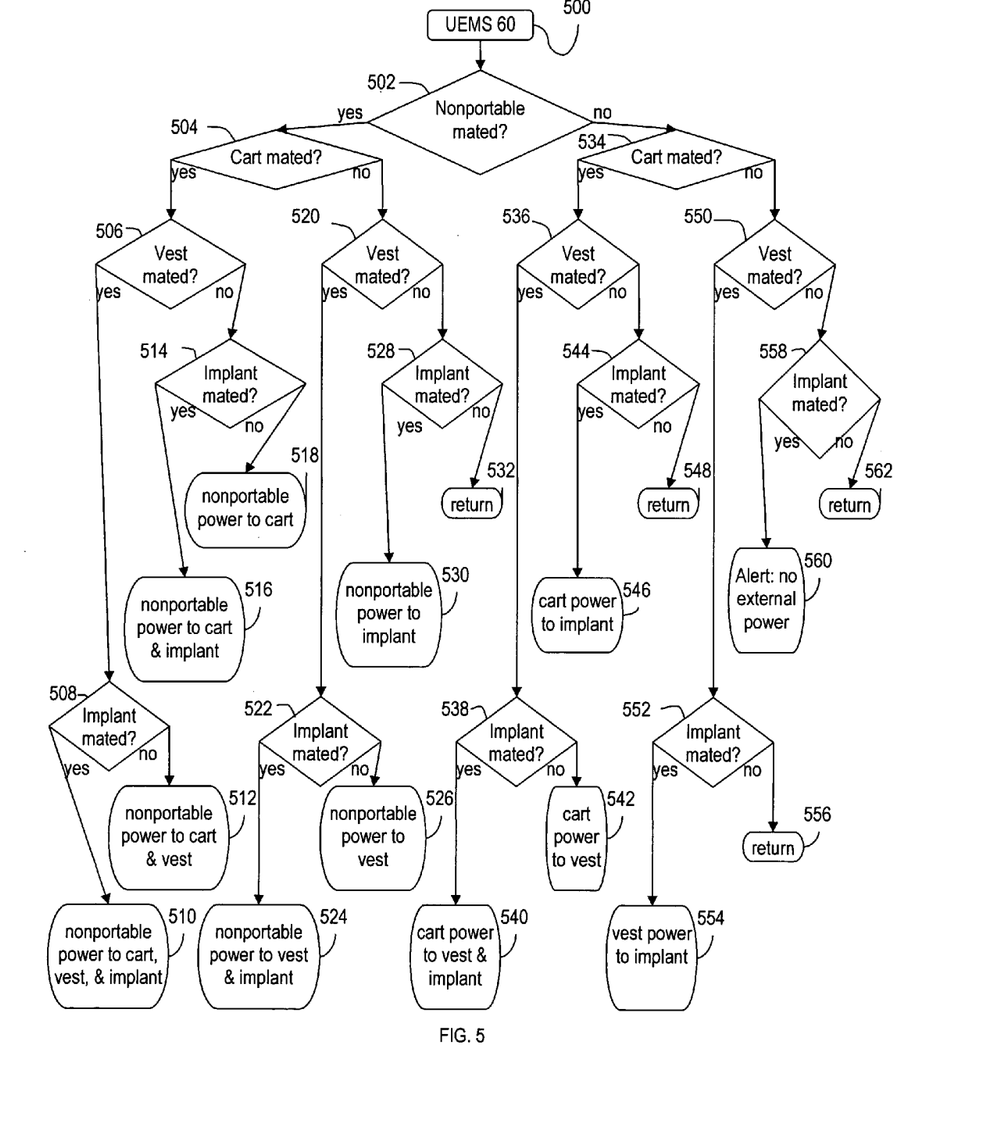
FIG. 5 is a flow chart showing the overall operation of the embodiment of FIG. 4.

In the embodiment of FIG. 1, an individual EMS provided in each power source, for example, Vest EMS 26, manages energy into and out of the power source and controls charging of the rechargeable battery 22. Alternatively, as shown in FIGS. 4 and 5 and described in relation thereto, there may be a universal energy management system (UEMS) that manages the energy to the implantable battery pack 10 and between the external power sources, while the individual energy management systems are used to control functions within an individual source, such as selecting from among primary and secondary batteries within a given source and providing a safety circuit.

The cart 30 is for long-term portable use and is designed to support a full day of operation until it needs recharging. Cart 30 may comprise only secondary, only primary, or some combination of primary and secondary power supplies. A cart having both battery types available uses Cart EMS 36 to intelligently manage the selection of one as a power source for device 50. Further, once a battery is selected as a power source, Cart EMS 36 also manages the transition from one to another type of battery in response to changes in device operating and/or environmental conditions. The cart 30 operates in normal environmental conditions and is easy for the patient to carry or roll along, similar to a rolling luggage cart. The cart 30 can also be used to recharge the vest 20 or implantable battery pack 10. For recharging vest 20, cart 30 can connect directly to vest 20 via a plug 39a to socket 21a; alternatively, primary coil 39 from cart 30 may mate with a secondary coil 21 from vest 20 for inductive charging.

Cart 30 is recharged by nonportable power system 40, either directly via a plug or inductively. Alternatively, cart 30 could be recharged using another portable energy source such as a vehicle battery or alternator (not shown) as described in U.S. Pat. No. 3,694,729. A small engine (internal combustion, Stirling, or other engine) driving a generator or alternator (not shown) may also be used for charging. Alternatively or additionally, photovoltaic cells (not shown) may be used as a tethered or semi-portable source of electricity.

The nonportable power source 40 can be used to recharge all of the smaller portable systems. It is the primary recharging station, comprising a permanent power supply, such as a wall socket 44, which preferably includes an uninterruptible power supply (UPS) 45. The nonportable power supply incorporates a Nonportable EMS 46.

Figure 2:
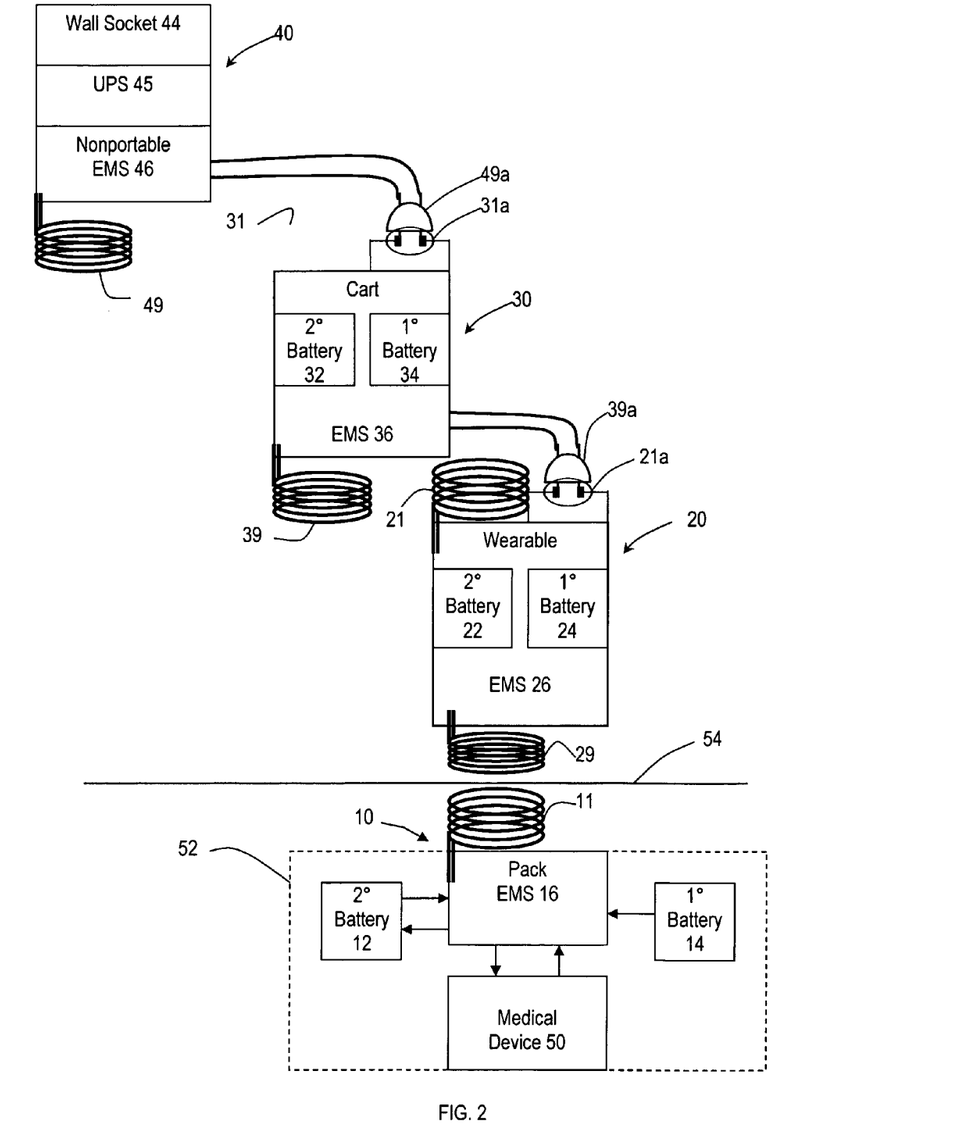
FIG. 2 is a schematic diagram of the embodiment of FIG. 1 showing an alternative arrangement of the various power sources.

FIG. 2 is a schematic diagram of the embodiment of FIG. 1 showing nonportable power source 40 coupled to cart source 30, which is coupled to wearable power source 20, which is coupled through the skin 54 to battery pack 10 and medical device 50 via primary coil 29 and secondary coil 11. Coupling between external components is preferably noninductive coupling, such as power outlet 49*a* to power inlet 31*a* or 21*a*, or power outlet 39*a* to power inlet 21*a*. Alternatively, inductive coupling may be used, such as primary coil 49 to secondary coil 31 or 21, or primary coil 39 to secondary coil 21.

Figure 3:
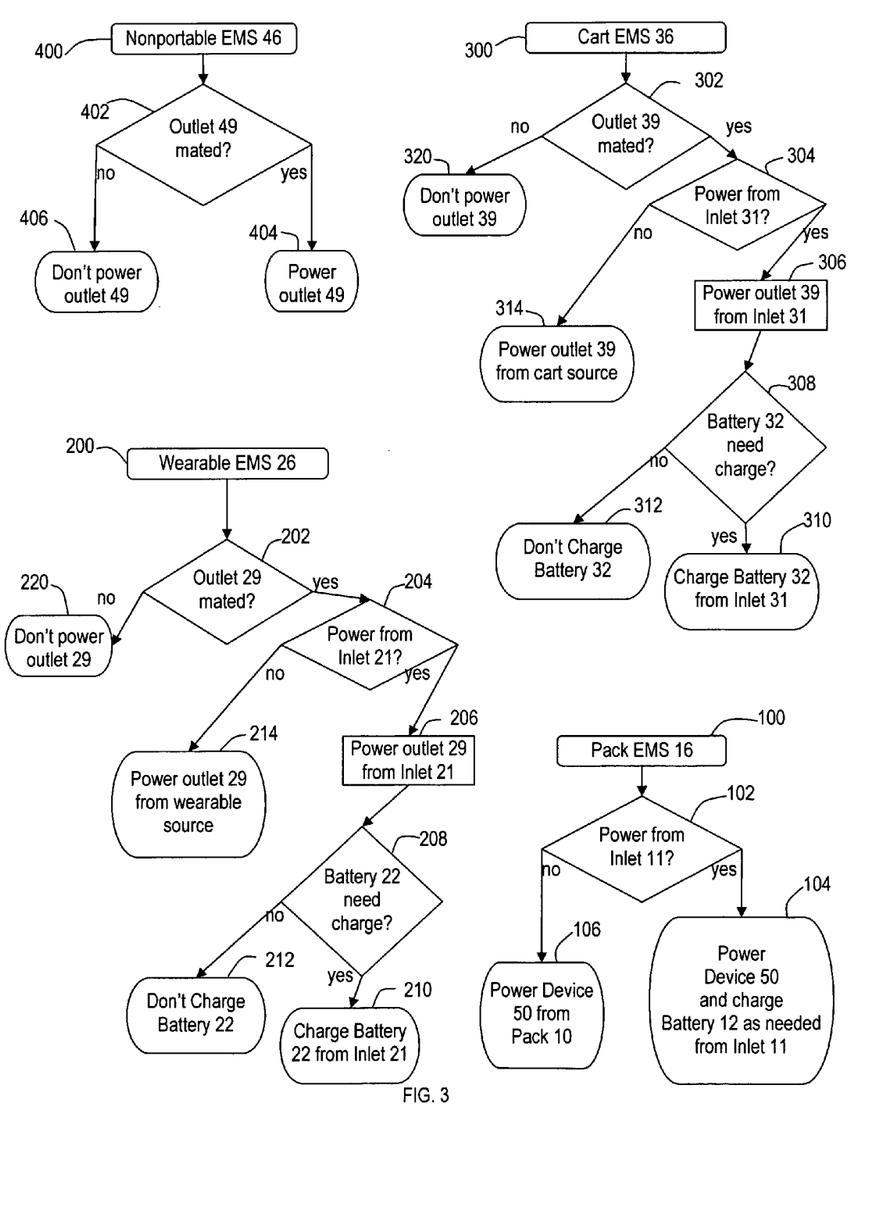
FIG. 3 is a flow chart showing the overall operation of the embodiment of FIGS. 1 and 2.

FIG. 3 is a flow chart showing a preferred method of the overall operation the embodiment of FIGS. 1 and 2. When the system is used with a nonportable power supply, the system is considered "tethered". Regulated power may be provided by such a tethered system indefinitely, at the cost of mobility. When one or more nonportable power supplies are present, they are preferentially chosen as the energy source to be utilized for power output. In case the nonportable power source should become unavailable or becomes inadequate for the power needs, the cart may be designated as the first backup power supply, and the vest as the second backup. Current available from the nonportable sources that is in excess of that needed to power the output device is used to maintain the charge on any secondary sources in the circuit (e.g. implantable pack battery 12, power cart battery 32, and wearable secondary batteries 22).

Starting at step 400, if the Nonportable EMS 46 detects in decision 402 that primary coil 49 is mated to secondary coil 11 or to a secondary coil of the cart or vest, the positive exit is taken and Nonportable EMS 46 sends power to the primary coil 49 at step 404. If primary coil 49 is not mated to a secondary coil, the negative exit is taken from decision 402 and power is not sent to the primary coil 49 at step 406. Likewise, if another power outlet 49*a* is connected to the cart or vest, Nonportable EMS 46 sends charging current to the cart or vest; if not, power is not sent to power outlet 49*a*. In an alternative embodiment, primary coil 49 and/or power outlet 49*a* may be continuously powered, and mating a secondary coil or plugging the outlet into an inlet completes the circuit to provide power from the nonportable power source, without relying on EMS 46 for this switching function depicted by decision 402.

At step 300, if the Cart EMS 36 detects in decision 302 that cart primary coil 39 is mated to pack secondary coil 11 or to a secondary coil 21, the positive exit is taken and Cart EMS 36 sends power to cart primary coil 39. If power is available from nonportable power source 40 at inlet 31, the positive exit is taken from decision 304 and power from the nonportable power source 40 at inlet 31 is used at step 306 to power primary coil 39 and recharge secondary battery 32 at step 310, if needed as determined at decision 308. If charging of secondary battery 32 is not needed, the negative exit is taken from decision 308 and battery 32 is not charged at step 312. At decision 304, if power is not available from the nonportable power source, the negative exit is taken and power from the cart itself is used to power cart primary coil 39. At decision 302, if primary coil 39 is not mated to a secondary coil, the negative exit is taken and Cart EMS 36 prevents power from being sent to the primary coil 39 at step 320. Likewise, if another power outlet 39*a* is connected to the vest, Cart EMS 36 sends charging current to the vest; if not, no power is sent to power outlet 39*a*. In an alternative embodiment, primary coil 39 and/or power outlet 39*a* may be continuously powered, and mating a secondary coil or plugging the outlet into an inlet completes the circuit to provide power, without relying on EMS 36 for this switching function depicted by decision 302.

At step 200, if the Wearable EMS 26 detects in decision 202 that vest primary coil 29 is mated to pack secondary coil 11, the positive exit is taken and Wearable EMS 26 sends power to vest primary coil 29. If power is available from inlet 21 either from cart 30 or from nonportable power source 40, the positive exit is taken from decision 204 and the power from inlet 21 is used to power primary coil 29. If battery 22 needs recharging, the positive exit is taken from decision 208 and battery 22 is charged from inlet 21 at step 210. If battery 22 does not need charging, the negative exit is taken from decision 208, and battery 22 is not charged in step 212. If power is not available from inlet 21, the negative exit is taken from decision 204, and outlet 29 is powered from the wearable power source. At decision 202, if vest primary coil 29 is not mated to a secondary coil, the negative exit is taken and power is not sent to primary coil 29 at step 220. In an alternative embodiment, primary coil 29 may be continuously powered, and mating a secondary coil completes the circuit to provide power to the implanted medical device 50 and recharge battery 12, without relying on EMS 26 for this switching function depicted by decision 202.

At step 100, if Pack EMS 16 detects that power is received by pack secondary coil 11, the positive exit from decision 102 is taken and Pack EMS 16 sends power from coil 11 to power medical device 50 and recharge battery 12 at step 104. If no power is received by coil 11, the negative exit from decision 102 is taken and Pack EMS 16 power from pack 10 to run medical device 50 at step 106. The power from pack 10 may be from rechargeable battery 12 as needed, if there is enough charge to run medical device 50. If not, primary battery 14 may be used to power medical device 50.

Note that nonportable power source 40 can recharge cart 30 while vest 20 powers medical device 50 and recharges implantable battery 12 as needed without requiring the patient to be tethered to the nonportable power source. Furthermore, nonportable power source 40 can recharge vest 20 while cart 30 powers medical device 50 and recharges implantable battery 12 without requiring the patient to be tethered to the nonportable power source. In addition, nonportable power source 40 can recharge both cart 30 and vest 20 while the implantable power pack 10 powers medical device 50. This flexibility allows for greater patient mobility and greater redundancy of power sources. Furthermore, the patient may be provided with two or more vests or with extra secondary batteries for a vest so that he always has a vest with charged batteries.

When nonportable power sources are not being used, the system can be operated as a mobile unit, relying exclusively on any combination of electrochemical storage devices. When multiple portable power sources are available away from nonportable power sources, as much as possible, the EMS supplies needed power from the largest sources in the system. Furthermore, within a single source, power is supplies preferentially from the primary battery while keeping the secondary battery charged, as taught in commonly owned Published PCT Patent Application WO 2004/027955 A2, which is incorporated herein by reference. During low to medium current draw applications, energy is conserved by using the primary battery to provide power to the output devices and charge the secondary battery. During mobile, high rate use, the secondary battery is used to provide power to the connected output device. Once the EMS senses the current draw change from high rate use to low or medium rate use, the EMS again conserves energy by switching to the primary battery to power the implanted medical device, charge the implanted battery, and charge the wearable secondary battery as needed. By having the ability to power the device by the primary source, the life of the rechargeable batteries may be prolonged by reducing the number of charging cycles. Once the EMS detects voltage loss in the primary batteries, it switches over to the secondary batteries, while continually supplying power to the medical device. If an extra primary battery is available, it can be inserted into the system when needed in order to preserve the secondary battery as a backup, while providing power from the new primary battery. This process of replacing primary batteries while maintaining prolonged periods of uninterrupted power could proceed indefinitely until the end of the rated lifetime of the secondary battery.

FIG. 4 is a schematic diagram of a second embodiment of the portable medical power system of the present invention having various power sources detachably attached to a universal energy management system (UEMS) 60. FIG. 4 shows an exemplary embodiment of UEMS 60 having first, second, and third power source connections, a power outlet 69, and a data relay 70. UEMS 60 can take in power from one or more connected power sources and supply power at multiple and customizable voltages. The UEMS power source connections each comprise power inlets 61a, 61b, 61c for receiving power from each of the detachably attached power sources. Additionally, one or more of the connectors may further comprise power outlets 69a, 69b for transmitting power through the UEMS for recharging any connected secondary sources. The inlets may connect the various power sources to the UEMS by continuous conductive paths, or by conductive paths that include inductive sections, or both. Similarly, the outlets may connect the various devices to the UEMS by continuous conductive paths, or by conductive paths that include inductive sections, or both. Inductive power source coupling is taught, for example, in Published PCT Patent Application WO 2004/027955 A2. UEMS 60 is able to identify the type of each attached power source by measuring the electrical characteristics such as internal resistance, momentary cell charging (characteristic dV/dt), or using mechanical means such as geometric characteristics of the power source connector, or any other means known in the art. UEMS 60 can then efficiently incorporate each source as needed, selectively routing power to implanted medical device 50 or for recharging any secondary battery in the system, including those in implanted or external power sources, or within the UEMS itself. Additionally, the system can be switched to manual control to suit specific situations.

UEMS 60 receives power from a nonportable source (wall socket or UPS which itself is connected to a wall socket), cart power source, or wearable power source, and provides power to an implanted medical device preferably via an inductive coil. The UEMS's internal logic and sensor system determines whether power will flow directly from the nonportable source or from an external portable source, such as the vest or cart. The UEMS then provides a fluctuating or pulsed current to the primary coil, to inductively power medical device 50 and/or recharge implantable secondary battery 12.

UEMS 60 may have separate inlets for receiving power in AC or DC form and for accepting various voltages and frequencies to fit the standards of different countries. Alternatively, the UEMS may be provided with a power source inlet that can receive power from nonportable power sources at various voltages and frequencies and manage the power to provide power to a connected device or to recharge an attached secondary battery. Furthermore, UEMS 60 may be standardized for use with various medical devices and may include a voltage regulator to provide multiple, constant, preprogrammed output voltages, for example, ranging from 1 V to 18 V, depending on power needs of implanted medical device 50. UEMS 60 may be used to provide external power to an implantable power module as described in Published PCT Patent Application WO 2004/027955 A2. UEMS 60 may itself be powered by a primary or secondary battery, or it may be powered by whatever power is connected to it.

UEMS 60 utilizes switching technology well known in the field of circuit design to efficiently utilize different types of energy sources and even individual batteries within a given energy source. UEMS 60 chooses the optimal power source for the output required of the connected device and to conserve rechargeable batteries within the system. UEMS 60 directs power to the device from any attached source, such as a nonportable source, a cart, or vest, based on which devices are connected and sufficiently charged. The system utilizes various available sources of energy based on output power requirements, recharging requirements, and preset selection of the available energy sources for given conditions. The energy source having the largest power available is used to power the device and charge the other rechargeable power sources. The optimum source is the tethered source when present, and, if the tethered source is not present, the optimum source is the cart power source if it is present and adequately charged, and, if the cart power source is not adequately charged, then the wearable power source is the optimum source if it is present and adequately charged; and if the wearable power source is not present or not adequately charged, the implantable power source is used to power the medical device. The UEMS may optionally include a warning system to notify the patient that no external sources remain in the system and that only implanted power is being used.

Redundancy is provided by the system, resulting in uninterrupted power even when changing batteries. In the preferred embodiment described above, during tethered use, any of the power source components or batteries within any of the power sources may be removed or swapped out without interruption of power and with power provided by the remaining sources or batteries within the sources during the transitions. For example, when the vest becomes unplugged, the system checks to see whether the nonportable power source or cart is connected; if it is not, the system switches to implantable power. The switching from one power source to another may be done gradually using any method known in the art, such as that taught in U.S. Pat. No. 4,851,756 to Schaller et al., which is hereby incorporated herein by reference.

UEMS 60 comprises a charge controller, which has the ability to charge an attached secondary battery from either a nonportable source or from an attached primary battery within a different source. The UEMS can direct power from a source to a device while the secondary battery is being charged by the same or a different source. The charge controller determines the charging current source and magnitude. By including a primary battery to charge the secondary batteries, the system allows for continuous charging and power. The UEMS can optimize the charging algorithm and charge state of the secondary battery. For example, the UEMS may allow the secondary battery to drain somewhat if it is better for the battery to not remain constantly fully charged.

Recharging of any secondary battery in the system can take place directly with a wired connection, or via an inductive couple. The system charges the rechargeable power source without requiring monitoring of the position of the primary coil in relation to the receiving coil and without interruption of power to the attached devices. This same pair of coils may be used for other communication between the charger and the battery, see e.g., U.S. Patent Publication US-2003-0085684-A1 and PCT Publication WO 014214 A2, which are assigned to the assignee of the present invention and incorporated herein by reference. Alternatively, a second pair of primary and secondary coils may be provided for communication without having to provide a complex algorithm to accommodate both functions on the same pair of coils. The coils may be located inside or outside the medical device.

The UEMS also provides protection against overcharge voltage, over discharge voltage, and excessive current draws. Furthermore, the power source (whether cart, vest, and/or implantable power supply) may be provided with a cooling system such as a fan, heat sink, water cooler, or other heat transfer device. The cart, in particular, may be provided with the cooling system taught in U.S. patent application Ser. No. 10/773,651, filed Feb. 6, 2004, entitled "Battery Cooling System and Coolant", which is assigned to the assignee of the present invention and incorporated herein by reference. These devices may optionally be furnished with an alarm or other warning system to communicate a warning message in the event that the temperature rises above a preset level, such as more than 5° C. above the surrounding environment.

UEMS 60 also can communicate directly with the Pack EMS 16 to provide information regarding remaining primary and secondary battery capacity, relevant status of medical device 50. Information regarding any of the connected sources can be sent from UEMS 60 to Pack EMS 16. Data, such as state of charge ("SOC"), remaining capacity, temperature, voltage, current, recharging status, and change of temperature or voltage with time (especially for NiCd or nickel metal hydride chemistries), preferably is obtained by either the UEMS or by the individual EMSes for both primary and secondary batteries. This information may be provided from a source EMS to the UEMS or vice versa, or directly between different connected source EMSes. This information may also be provided via a data relay 70 to the end user by a diagnostic LED array located on the UEMS itself or remotely such as on a wearable wireless readout. Alternatively, data relay 70 may relay the data to any directly or remotely connected device. The display can communicate battery parameters including, but not limited to, voltage, state of charge, current draw, temperature, and time to empty.

FIG. 5 is a flow chart showing the overall operation of the embodiment of FIG. 4. In this case, the universal energy management system (UEMS) 60 monitors and manages energy throughout the power system, preferentially selecting the largest power sources as available and charging secondary batteries from larger sources and/or primary sources as needed. Preferably, the individual energy management system (EMS) within each component, such as EMS 36, EMS 26, and EMS 16, determines from which source, such as primary or secondary, to send power to smaller components. Alternatively, UEMS 60 may have multiple inlets from a given component, corresponding to power lines from multiple sources within a component. In that case, UEMS 60 may determine from which source to receive power from the component. For example, although not shown in FIG. 4, cart source 30 may have separate power lines coming from secondary battery 32 and primary battery 34 to UEMS 60. In that case, UEMS 60 can determine from which cart power source battery to accept power. Likewise, the functionality of charging may reside within UEMS 60, within each individual EMS, or within a combination. For example, when using a larger source to recharge a secondary battery within a smaller source, UEMS 60 may be used to regulate the charging, and when using a primary battery to recharge a secondary battery within a single source, the individual EMS may be used to regulate the charging. It should be noted that although an individual EMS is shown for each power source, in some embodiments, the individual sources do not have an EMS, or the EMS consists of a safety circuit, with all other energy management function residing in the UEMS.

As shown in FIG. 5, beginning at step 500, UEMS 60 determines at decision 502 whether power is available from a nonportable source. If so, the positive exit is taken, and UEMS 60 determines at decision 504 whether power is available from a cart power source. If so, the positive exit is taken and UEMS 60 determines at decision 506 whether power is available from a vest power source. If so, the positive exit is taken and UEMS 60 determines at decision 508 whether an implanted device is mated. If so, power from the nonportable power source is sent to the cart, vest, and implant at step 510 for powering the implanted medical device and recharging any secondary power sources within the cart, vest, or implant as needed. At decision 508, if no implant is mated with UEMS 60, the negative exit is taken and power from the nonportable power source is sent to the cart and vest for recharging any secondary power sources within them as needed. At decision 506, if no power is available from a vest source, the negative exit is taken and UEMS 60 determines at decision 514 whether an implanted device is mated. If so, power from the nonportable power source is sent to the cart and implant at step 516 for powering device 50 and recharging any secondary power sources within the cart or implant as needed. At decision 514, if no implant is mated with UEMS 60, the negative exit is taken and power from the nonportable power source is sent to the cart for recharging any secondary power sources as needed at step 518. At decision 504, if no power is available from a cart source, the negative exit is taken and UEMS 60 determines at decision 520 whether power is available from a vest power source. If so, UEMS 60 determines at decision 522 whether an implant is mated. If so, the positive exit is taken and power from the nonportable power source is used to power the medical device and charge any secondary sources in the vest and implant as needed at step 524. If no implant is mated with UEMS 60, the negative exit is taken and power from the nonportable power source is used to recharge any secondary sources in the vest as needed at step 526. At decision 520, if the vest is not mated with UEMS 60, UEMS 60 determines at decision 528 whether an implant is mated. If so, the positive exit is taken and power from the nonportable power source is used to power the implanted medical device and recharge any secondary sources within it as needed at step 530. If at decision 528, it determines that no implant is mated, UEMS 60 continues to monitor the status of connected sources at step 532.

At step 502, if UEMS 60 determines that no power is available from a nonportable power source, the negative exit is taken and UEMS 60 determines at decision 534 whether power is available from a cart power source. If so, the positive exit is taken and at decision 536 UEMS 60 determines whether a vest power source is mated. If so, the positive exit is taken and UEMS 60 determines at decision 538 whether an implant is mated. If so, the positive exit is taken and at step 540, power from the cart power source is used to power the implanted medical device and to recharge any secondary sources within the vest and implant as needed. If no implant is mated, the negative exit is taken and at step 542, power from the cart is used to recharge any secondary sources in the vest as needed. If at decision 536, it is determined that there is no vest mated, the negative exit is taken and UEMS 60 determines at decision 544 whether an implant is mated. If so, the positive exit is taken and at step 546, power from the cart is used to power the implanted medical device and charge secondary sources within the implant as needed. If no implant is mated at decision 544, the negative exit is taken and UEMS 60 continues to monitor. If at decision 534, UEMS 60 determines that no power is available from a cart power source, the negative exit is take, and UEMS 60 then determines at decision 550 whether power is available from a vest power source. If so, the positive exit is taken, and if an implant is detected at decision 552, power from the vest is used to power the medical device and charge implanted secondary sources as needed in step 554. If no implant is detected at decision 552, the negative exit is taken and monitoring continues at step 556. If at step 550, UEMS 60 determines that no power is available from a vest power source, the negative exit is taken and UEMS 60 determines whether an implant is mated at decision 558. If so, the positive exit is taken and UEMS 60 alerts the patient that no external power is available and that the implanted device is running solely on its own power. If no implant is detected at decision 558, the negative exit is taken and UEMS 60 continues to monitor.

The specific implementations disclosed above are by way of example and for enabling persons skilled in the art to implement the invention only. We have made every effort to describe all the embodiments we have foreseen. There may be embodiments that are unforeseeable or which are insubstantially different. We have further made every effort to describe the methodology of this invention, including the best mode of practicing it. Any omission of any variation of the method disclosed is not intended to dedicate such variation to the public, and all unforeseen or insubstantial variations are intended to be covered by the claims appended hereto. Accordingly, the invention is not to be limited except by the appended claims and legal equivalents.

What is claimed is:

1. A power system for powering an implantable medical device, comprising:
an implantable battery pack including an implantable secondary battery and an implantable energy management system for controlling power to the medical device and to the secondary battery;
an implantable power inlet for receiving power to charge the secondary battery; and
nonimplantable power sources that are each configured to provide the power for charging the secondary battery to the power inlet without that power flowing from the power source to the power inlet through another one of the power sources,
at least one of the nonimplantable power sources being a nonportable power source configured to be plugged directly into a wall socket,
at least one other nonimplantable power source being chosen from the group consisting of: a wearable power source configured to receive electrical power from the nonportable power source, and a power cart configured to receive electrical power from the nonportable power source.

2. The power system of claim 1, wherein the implantable power inlet includes a coil for inductive power reception.

3. The power system of claim 1, wherein one of the nonimplantable power sources included in the power system is the wearable power source and the wearable power source includes an energy storage device in communication with a power outlet configured to send energy from the energy storage device to the implantable battery pack.

4. The power system of claim 3, wherein the power outlet included in the wearable power source includes a coil for inductive transmission of power from the wearable power source.

5. The power system of claim 1, wherein one of the nonimplantable power sources included in the power system is the wearable power source and the wearable power source includes a secondary battery and a power inlet for receiving power from at least one source selected from a group consisting of the nonportable power source and the power cart, the wearable power source configured to employ the power received at the inlet that is included in the wearable power source to charge the secondary battery.

6. The power system of claim 1, wherein one of the nonimplantable power sources included in the power system is the power cart and the power cart includes an energy storage device and a power outlet for sending power from the energy storage device to at least one source selected from a group consisting of the implantable battery pack and the wearable power source.

7. The power system of claim 6, wherein the power outlet included in the power cart includes a coil for inductive transmission of the power from the energy storage device.

8. The power system of claim 1, wherein one of the nonimplantable power sources included in the power system is the power cart and the power cart includes a secondary battery and a power inlet for receiving power from the nonportable power source, the power cart configured to employ the power received from the nonportable power source to charge the secondary battery included in the power cart.

9. The power system of claim 1, wherein a power outlet included in the nonportable power source includes an inductive coil.

10. The power system of claim 1, further comprising:
a universal energy management system (UEMS) having logic for selecting one of the nonimplantable power sources from among the nonimplantable power sources included in the power system.

11. The power system of claim 10, wherein one of the nonimplantable power sources included in the power system is the wearable power source and the UEMS is located in the wearable power source.

12. The power system of claim 10, wherein the logic for selecting one of the nonimplantable power sources selects the nonimplantable power source to be used for powering the implantable medical device.

13. The power system of claim 10, wherein logic for selecting one of the nonimplantable power sources selects the nonimplantable power source to be used for charging the implantable secondary battery included in the implantable battery pack.

14. The power system of claim 13, wherein the UEMS includes a charge controller for controlling the magnitude of the charging current to the secondary battery included in the implantable battery pack.

15. The power system of claim 10, wherein the secondary battery included in the implantable battery pack is one of a plurality of batteries connected to the UEMS and the energy management system includes a measuring device for measuring remaining charge in at least one of the batteries connected to the UEMS.

16. The power system of claim 1, wherein the implantable battery pack includes a primary battery.

17. The power system of claim 1, wherein the power cart and the nonportable power source each includes a primary battery and a secondary battery.

18. The power system of claim 1, wherein the power cart is configured to be recharged by the electrical power received from the nonportable power source and the wearable power source is configured to be recharged by the electrical power received from the nonportable power source.

19. The power system of claim 1, wherein a secondary battery included in the power cart is configured to be recharged by the electrical power received from the nonportable power source and a secondary battery included in the wearable power source is configured to be recharged by the electrical power received from the nonportable power source.

* * * * *